(12) United States Patent
Dijkstra et al.

(10) Patent No.: US 11,376,186 B2
(45) Date of Patent: Jul. 5, 2022

(54) PHOTOTHERAPY BODY ROLLER

(71) Applicant: LIGHT TREE, Amstelveen (NL)

(72) Inventors: Alain Dijkstra, Amstelveen (NL); Yvonne Johanna Margaretha Houthuijs, Amstelveen (NL)

( * ) Notice: Subject to any disclaimer, the term of this patent is extended or adjusted under 35 U.S.C. 154(b) by 624 days.

(21) Appl. No.: 16/377,235

(22) Filed: Apr. 7, 2019

(65) Prior Publication Data
US 2020/0315907 A1 Oct. 8, 2020

(51) Int. Cl.
| | |
|---|---|
| A61H 15/00 | (2006.01) |
| A61H 15/02 | (2006.01) |
| A61N 5/06 | (2006.01) |
| A61H 23/00 | (2006.01) |

(52) U.S. Cl.
CPC .......... *A61H 15/02* (2013.01); *A61H 15/0092* (2013.01); *A61H 23/00* (2013.01); *A61N 5/0616* (2013.01); *A61H 2015/0014* (2013.01); *A61H 2201/10* (2013.01); *A61H 2201/5028* (2013.01); *A61N 2005/0626* (2013.01); *A61N 2005/0633* (2013.01); *A61N 2005/0644* (2013.01); *A61N 2005/0652* (2013.01)

(58) Field of Classification Search
CPC .... A61H 15/00; A61H 15/02; A61H 15/0092; A61H 2015/0014; A61H 2201/10; A61N 5/00; A61N 5/06; A61N 2005/0643; A61N 2005/0644; A61N 2005/065; A61N 2005/0651; A61N 2005/0652; A61N 2005/0653; A61N 2005/0654; A61N 2005/0655; A45D 34/04; A45D 34/041
See application file for complete search history.

(56) References Cited

U.S. PATENT DOCUMENTS

| | | | | |
|---|---|---|---|---|
| 1,965,918 | A * | 7/1934 | Auberger | A61H 15/02 601/119 |
| 2,307,554 | A * | 1/1943 | Wettlaufer | A61H 23/0263 601/72 |
| 2,537,037 | A * | 1/1951 | Curtis | A61H 15/02 601/19 |
| 2,628,611 | A * | 2/1953 | Wagner | A61H 15/0092 601/120 |
| 2,647,509 | A * | 8/1953 | Studler | A61H 15/0092 601/19 |
| 2,795,224 | A * | 6/1957 | Brandenburg | A61H 23/0218 601/18 |
| 3,845,758 | A * | 11/1974 | Anderson | A61H 15/0085 601/114 |
| 5,637,065 | A * | 6/1997 | Chang | A63B 23/14 482/1 |
| 9,968,513 | B1 | 5/2018 | Marton et al. | |

(Continued)

*Primary Examiner* — Justine R Yu
*Assistant Examiner* — Christopher E Miller
(74) *Attorney, Agent, or Firm* — Willie Jacques; Emanus, LLC (57) ABSTRACT

A phototherapy body roller which includes a rotatable outer casing having at least one transparent portion. The phototherapy body roller can perform LED light therapy while using as a body roller for self-exercise, stretching, fascia and relieve fatigue and relax muscle groups. With a balancing device, the light source is always facing the upper part of the phototherapy body roller, which saves energy and does not cause light pollution, and is environmentally friendly.

9 Claims, 6 Drawing Sheets

(56) References Cited

U.S. PATENT DOCUMENTS

| | | | |
|---|---|---|---|
| 2006/0183072 A1* | 8/2006 | Black | A61N 5/0613 433/29 |
| 2008/0262394 A1* | 10/2008 | Pryor | A61N 5/0613 601/15 |
| 2015/0165238 A1* | 6/2015 | Slayton | A61B 18/1815 601/2 |
| 2017/0106249 A1* | 4/2017 | Marton | A63B 43/004 |
| 2017/0216136 A1* | 8/2017 | Gordon | A61H 15/0092 |
| 2018/0008512 A1* | 1/2018 | Goldstein | A61N 2/002 |
| 2018/0037293 A1* | 2/2018 | Chen | B62J 43/20 |
| 2018/0049941 A1* | 2/2018 | Venezia | A61H 15/02 |

* cited by examiner

PHOTOTHERAPY BODY ROLLER

FIELD OF THE DISCLOSURE

Various embodiments of the disclosure relate to a phototherapy body roller. More specifically, various embodiments of the disclosure relate to sports utility body roller for providing phototherapy and body massaging to a user.

BACKGROUND

Every day people incur injuries and ailments to various parts of their bodies and seek therapy from a number of sources including doctors, physical therapists, masseuses, and/or by using at-home therapeutic devices. With the continuous improvement of living standards, people pay more attention to physical health, yoga and other sports bodybuilding activities have been favored by people. Body rollers are ideal for yoga practitioners. The body rollers can help the yoga practitioner to complete various balancing actions, which can eliminate muscle tension, strengthen the core muscles, achieve a balance of exercise, and reduce body fat. At present, there are many types of body rollers are available which are generally same in shape and are used in a certain way, most of the body rollers available are having an outer surface that is made of soft material or some massage particles are added on the outer surface to increase the massage effect. The present invention provides a phototherapy body roller that is in general, of same shape and size as the existing body rollers, but also provides light therapy with body massage and helps in skin rejuvenation, healing body dysfunction blood flow etc.

Further, in the prior art, various types of body rollers are proposed with different functionality and method of use but none of these body rollers are as useful and health benefit as the present invention, some of the prior art patents for the body rollers for reference are as mentioned below:

In another U.S. Pat. No. 9,968,513B1 Robert Marton et. al, discloses a portable vibrating roller includes an outer roller structure having a plurality of grooves and ribs. A hollow cylindrical bore extends longitudinally through the shell. A vibration system having a first end cap and a second end cap fits within the bore. A battery positioned within the shell near one end cap provides electrical power to a motor positioned within the shell near the other end cap to cause the motor to rotate an output shaft at a plurality of angular velocities to rotate an eccentric mass located approximately midway between the two end caps. Hence, the prior art not providing a body roller for light therapy and massaging in a single unit like the present invention Thus, the currently available body rollers have a single function and can only exercise the muscles, and has no effect on the skin whitening or wrinkle reduction, skin rejuvenation, and muscle stimulation etc. When people use body roller for muscle exercise, they also need make efforts to take light therapy separately, and the time during the exercise is not fully utilized.

None of the body rollers available in the prior art are able to provide light therapy and massaging function at the same time or does not provide multifunction facility.

Further, limitations and disadvantages of conventional and traditional approaches will become apparent to one skilled in the art, through comparison of described systems with some aspects of the present disclosure, as set forth in the remainder of the present application and with reference to the drawings.

SUMMARY

In view of the foregoing disadvantages inherent in the prior art and the needs as mentioned above, the general purpose of the present disclosure is to provide a phototherapy body roller that can overcome the disadvantages of the prior art.

The Briefly and in general terms, the present disclosure is directed towards a body roller device that can provide massage and phototherapy as well. In one aspect, the phototherapy body roller includes a rotatable outer casing of cylindrical or spherical shape and at least a portion of the outer casing is transparent. Further, the outer casing is a hollow and rigid cylindrical body including a light board and a power supply unit for supplying power to the light board are installed therein, and the light board is mounted on a balancing assembly. Furthermore, the light emitting tubes mounted on the light board are continually facing towards the transparent portion of the outer casing irrespective of the outer casing rotation.

The present disclosure has beneficial effects compared with the prior art, the phototherapy body roller is provided with a light board for phototherapy and can perform LED (Light Emitting Diode) phototherapy while using the body roller for self-exercise stretching fascia to relieve fatigue and relax the muscle group, and the phototherapy can not only whiten the skin but also relieve the movement. Causes muscle damage, prevents muscle swelling, promotes blood circulation, relieves fatigue and pain, and enhances joint flexibility.

A balancing device is provided to make the light source always face the upper part of the phototherapy body roller. The illumination range of the light is only for the body part that needs to be stretched, which saves energy and does not cause light pollution, and is healthy and environmentally friendly. The phototherapy body roller can be used in various health and sports fields, such as yoga, rehabilitation exercise, personal training, etc., and is particularly effective for people with poor blood circulation, frequent swelling of the legs and cramps, and people who are sedentary and have heavy limbs.

According to various aspect of the present disclosure, when the skin is exposed to light radiation, which typically includes wavelengths that are absorbed by a chromophore (e.g. melanin, hemoglobin) present in the skin the incident energy can be converted to heat. If sufficient energy is absorbed, one or more benefits to the skin can be imparted, such as reduced age spots, reduced pigmentation of the spots, reduced wrinkles, reduced vascular system, reduced skin roughness, and reduced skin relaxation. Certain spectra emitted by LEDs (blue or red) are therapeutic for skin treatments such as acne or beneficial for inhibiting skin aging. The basic premise of light-based treatment is that different wavelengths trigger different reactions under the epidermis and penetrate the skin at different depths until it affects blood vessels and bones in the skin. Blue light is commonly used to kill bacteria that cause acne, providing effective treatment for blackheads and whiteheads, while red light wavelengths are often used to accelerate healing and stimulate collagen production while reducing pore size and tightening the skin.

These and other features and advantages of the present disclosure may be appreciated from a review of the following detailed description of the present disclosure, along with

DETAILED DESCRIPTION

Embodiments of the present disclosure will be described more fully hereinafter with reference to the accompanying drawings in which like numerals represent like elements throughout the figures, and in which example embodiments are shown.

The detailed description and the drawings illustrate specific exemplary embodiments by which the disclosure may be practiced. These embodiments are described in detail to enable those skilled in the art to practice the disclosure. It is understood that other embodiments may be utilized, and other changes may be made, without departing from the spirit or scope of the present disclosure. The following detailed description is therefore not to be taken in a limiting sense, and the scope of the present disclosure is defined by the appended claims. Embodiments of the claims may, however, be embodied in many different forms and should not be construed as limited to the embodiments set forth herein.

Embodiments of the disclosure are discussed below with reference to the Figures. However, those skilled in the art will readily appreciate that the detailed description given herein with respect to these figures is for explanatory purposes as the disclosure extends beyond these limited embodiments. For example, it should be appreciated that those skilled in the art will, in light of the teachings of the present disclosure, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the disclosure that are too numerous to be listed but that all fit within the scope of the disclosure. Also, singular words should be read as plural and vice versa and masculine as feminine and vice versa, where appropriate, and alternative embodiments do not necessarily imply that the two are mutually exclusive.

It is to be further understood that the present disclosure is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present disclosure. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this disclosure belongs. Preferred methods, techniques, devices, and materials are described, although any methods, techniques, devices, or materials similar or equivalent to those described herein may be used in the practice or testing of the present disclosure. Structures described herein are to be understood also to refer to functional equivalents of such structures. The present disclosure will now be described in detail with reference to embodiments thereof as illustrated in the accompanying drawings.

References to "one embodiment," "an embodiment," "example embodiment," "various embodiments," etc., may indicate that the embodiment(s) of the disclosure so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

The foregoing descriptions of specific embodiments of the present disclosure have been presented for purposes of illustration and description. They are not intended to be exhaustive or to limit the invention to the precise forms disclosed, and obviously many modifications and variations are possible in light of the above teaching. The exemplary embodiment was chosen and described in order to best explain the principles of the invention and its practical application, to thereby enable others skilled in the art to best utilize the invention and various embodiments with various modifications as are suited to the particular use contemplated.

Figure 1:
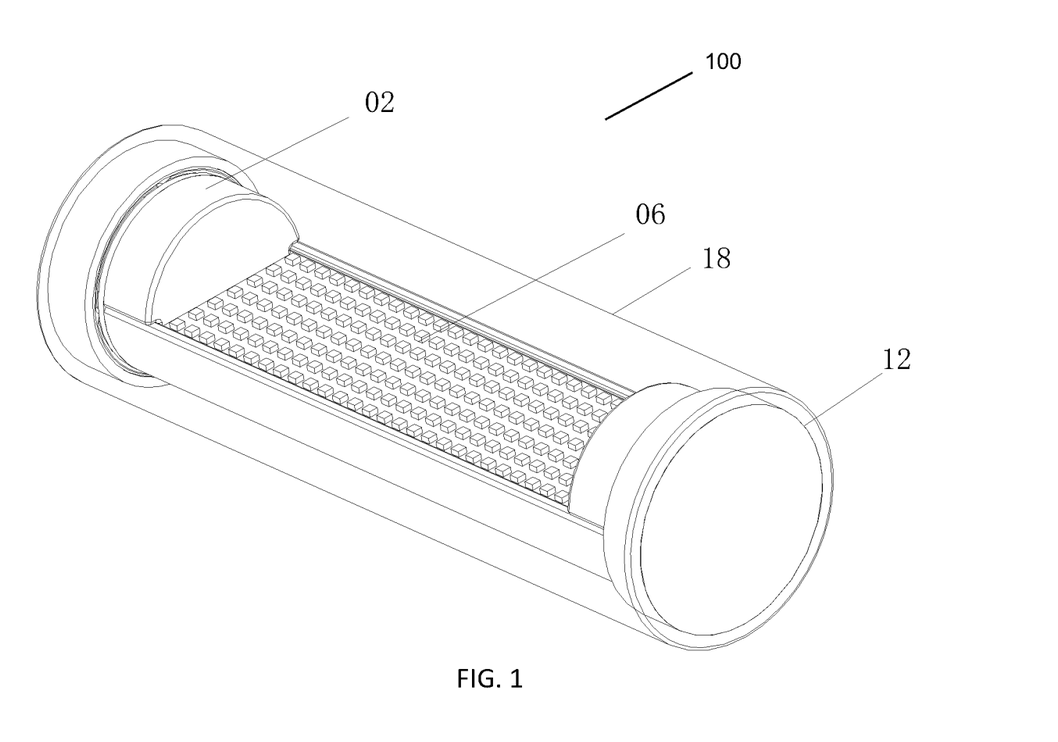
FIG. 1 is an isometric view of a phototherapy body roller according to a first embodiment of the present disclosure.
Figure 2:
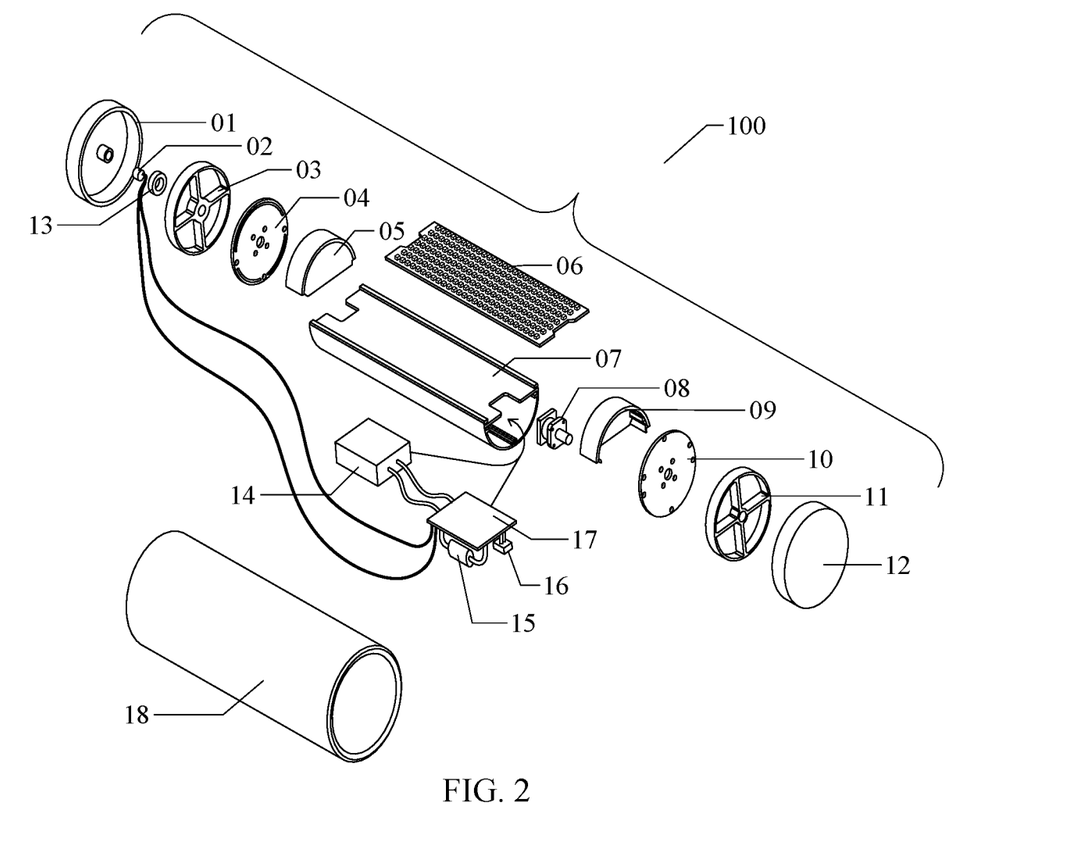
FIG. 2 is an exploded view of the phototherapy body roller according to the first embodiment of the present disclosure.
Figure 3:
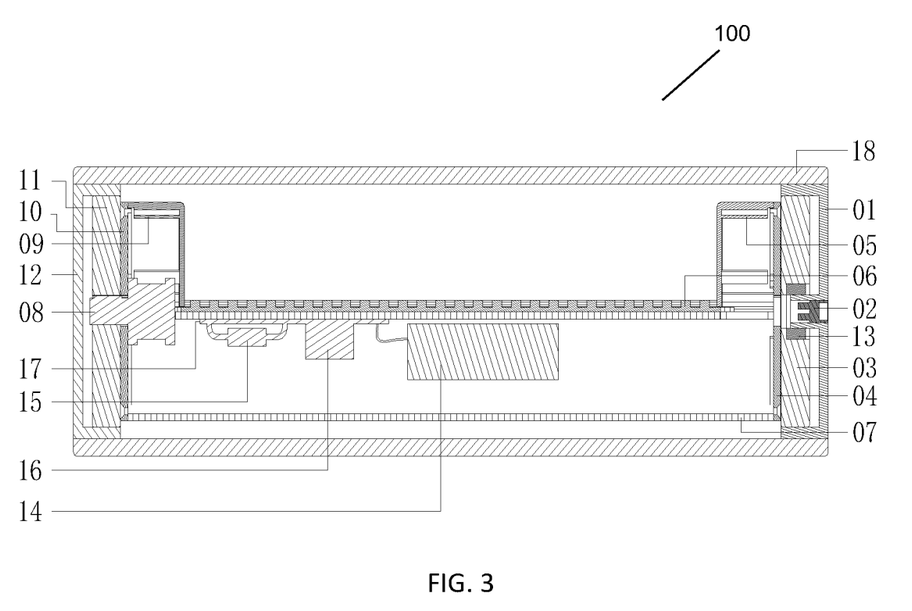
FIG. 3 is a cross-sectional view of the phototherapy body roller according to the first embodiment of the present disclosure.

Referring to FIG. 1 to FIG. 3, a phototherapy body roller 100 is shown according to a first embodiment of the present disclosure. The phototherapy body roller 100 includes a left cover 01, a power interface 02, a left turntable 03, a left fixed plate 04, a left cap 05, a light board 06, a light housing 07, and a motor 08. Further, the phototherapy body roller 100 includes a right cap 09, a right fixed plate 10, a right turntable 11, a right cover 12, a bearing 13, a battery 14, a power switch 15, a gyroscope 16, a control board 17, and an outer casing 18. The power interface 02, the battery 14, the power switch 15, and the control board 17 are connected by wires, and the power supply unit is configured to supply power to the light board 06. The left turntable 03, the right turntable 11, the bearing 13, the battery 14, and the gyroscope 16 constitute a balancing device, and the balancing device functions to ensure that the light emitting surface of the light plate 06 is always facing upward.

The left cover 01 is made of a metal material, surrounded by a cap, and has a mounting post at the center shaft. The outer ring of the cap is fixedly mounted to the outer casing 18, and the inner ring of the cap is assembled with the left turntable 03. Further, the mounting post extends into the inner ring of the bearing 13 and is mated with the inner ring of the bearing 13, the left cover 1 and the left turntable 03 are assembled at the mirror surface to allow the bearing 13 and the left turntable 03 to rotate about their central axes.

The power interface 02 is a safe low-voltage current input interface that supplies power to the entire power supply unit to charge the battery 14.

The center column of the left turntable 03 is assembled with the bearing 13, and the outer ring is mirror-polished to minimize friction and is rotated by the right turntable.

The left fixing plate 04 is used to fix the left cap 05 and the light housing 07. The left cap 05 serves as a covering function to cover the power cord and the like.

The light board 06 is formed by welding LED lamps or infrared lamps or laser diodes such as a laser diode on the heat dissipating aluminum substrate, and the light emitting tube faces the outer casing 18 that is made of transparent material. The left and right center line of the light board 06 is consistent with the central axis of rotation of the left turntable 03 and the right turntables 11, and when the left turntable 03 and the right turntables 11 are rotated the center axis position remains unchanged, so that the centerline position of the light board 06 will not change.

The light housing 07 is used for fixing the light board 06, and has a high heat dissipation coefficient metal material and is light in weight.

The output shaft of the motor 08 is fixedly linked to the right rotary disk or right turntable 11, and the motor 08 detects the data by the gyroscope 16 to perform the position adjustment operation of the light board 06.

The right cap 09 serves as a covering function to cover the power cord and the motor 08. The right fixed plate 10 is used to fix the right cap 09 and the light housing 07 and the motor 08.

The right turntable 11 is coupled to the output shaft of the motor 08 and is driven to rotate by the motor 08. The surface friction is small and light.

The right cover 12 is mirror-polished with a metal material which allows the right turntable 11 to operate at high speed and is surrounded by a cap and a mounting hole at the center shaft. The outer ring of the cap is fixedly mounted to the outer casing 18, and the inner ring of the cap is assembled with the right rotary disk or right turntable 11. The mounting hole is assembled with the output shaft of the motor 08. The mirror assembly polishing process is performed on the assembly of the right cover 12 and the right turntable 11 so that the right turntable 11 can be rotated about the central axis by the motor 08. Further, since the right turntable 11 is fixedly attached to the right fixed plate 10, the light housing 07, the left fixed plate 04, and the left turntable 03 thus the rotation of the right turntable 11 also drives the left turntable 03 to rotate.

The outer ring of the bearing 13 is fixedly mounted to the left turntable 03 and the inner ring of the bearing 13 is fixedly mounted with the left cover 01. Further, the bearing1 3 can be rotated at a high speed and has a small volume and a long service life.

The battery 14 is made of a high polymer battery, has a small volume and a large capacity, and has a high safety factor of explosion protection, and is charged through the power interface 02.

The power switch 15 uses a vibration switch, which generates vibration when the phototherapy body roller 100 rotates, thereby starting up, and the software loaded on a central microprocessor mounted on the control board 17 sets the working time and program after the power is turned on. The power switch 15 can also adopt a touch switch and can be turned on by a skin touch, and the touch switching is high in sensitivity and high in reliability. The power switch 15 can also be a pressure sensor switch. When using the phototherapy body roller 100 the human body will be pressed on the phototherapy body roller 100 and is turned on by the touch force.

The gyroscope 16 and the light board 06 are fixedly mounted, and a solid-state gyroscope or an electronic gyroscope can be used to detect the angle change and the displacement amount of the light board 06. Further, the motor 08 is operated after receiving the output of the control board 17, in a way so that the light board 06 is always upward.

The control board 17 is loaded with control software, including a sophisticated and high-speed central microprocessor and its electronic components.

The outer casing 18 is a fully transparent outer casing, which adopts a highly transparent soft material to meet biocompatibility requirements and is in comfortable contact with human skin.

When in use, the outer casing 18 rotates to drive the left cover 01 and right cover 12 that makes the light board 06 and the left turntable 03 and right turntable 11 inside the outer casing 18 rotate. Further, the gyroscope 16 detects the angle change and the displacement amount of the light board 06 and then outputs a signal to the control board 17, and the motor 08 operates to drive the left turntable 03 and right turntable 11. The left turntable 03 and right turntable 11 are also able to rotate in the reverse direction so that the direction of the light board 06 remains unchanged.

Figure 4:
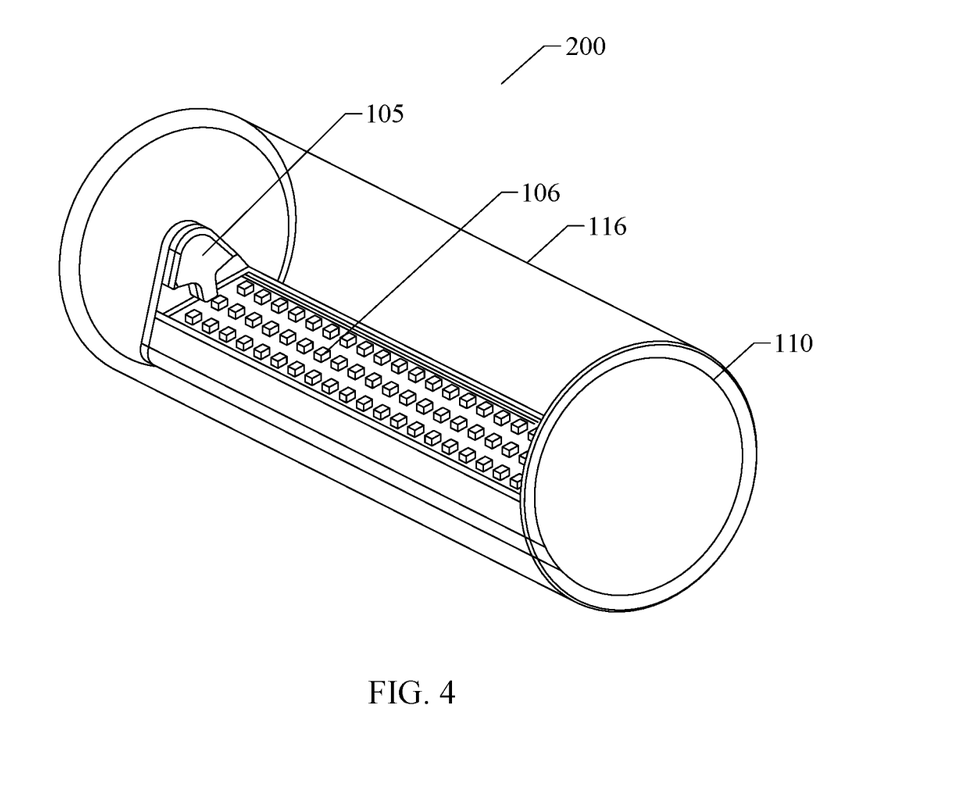
FIG. 4 is an isometric view of a phototherapy body roller according to a second embodiment of the present disclosure.
Figure 5:
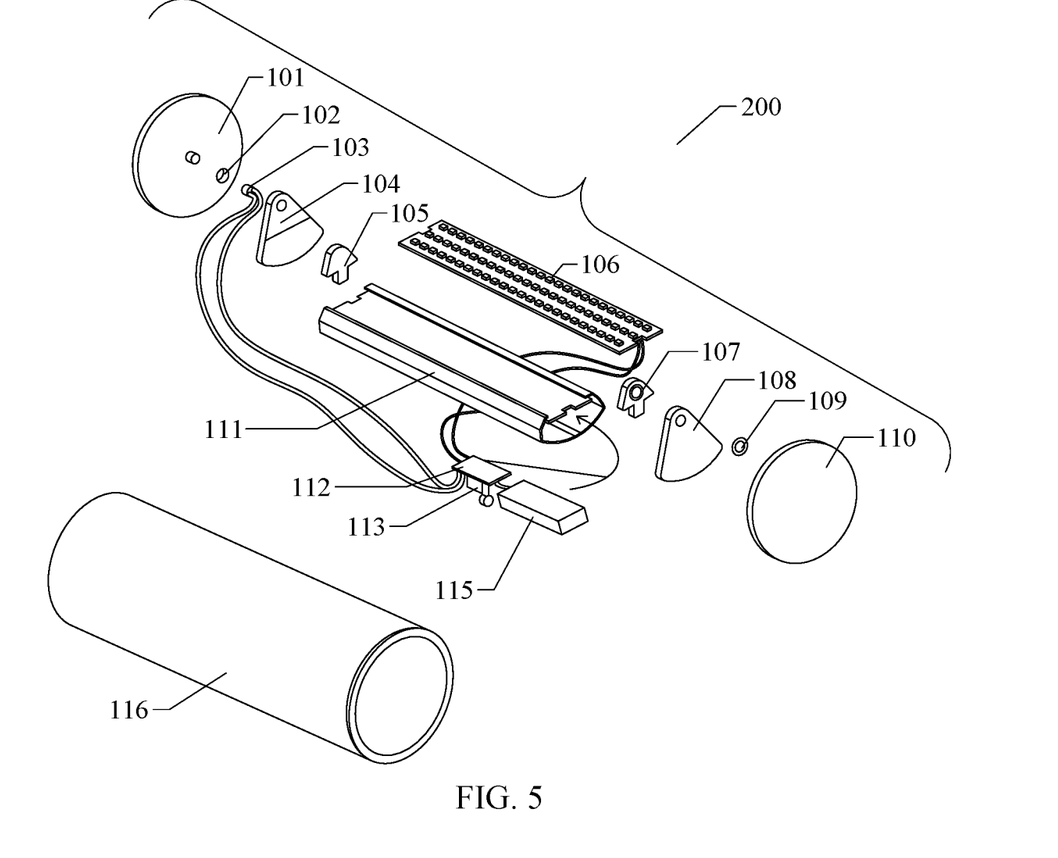
FIG. 5 is an exploded view of the phototherapy body roller according to the second embodiment of the present disclosure.
Figure 6:
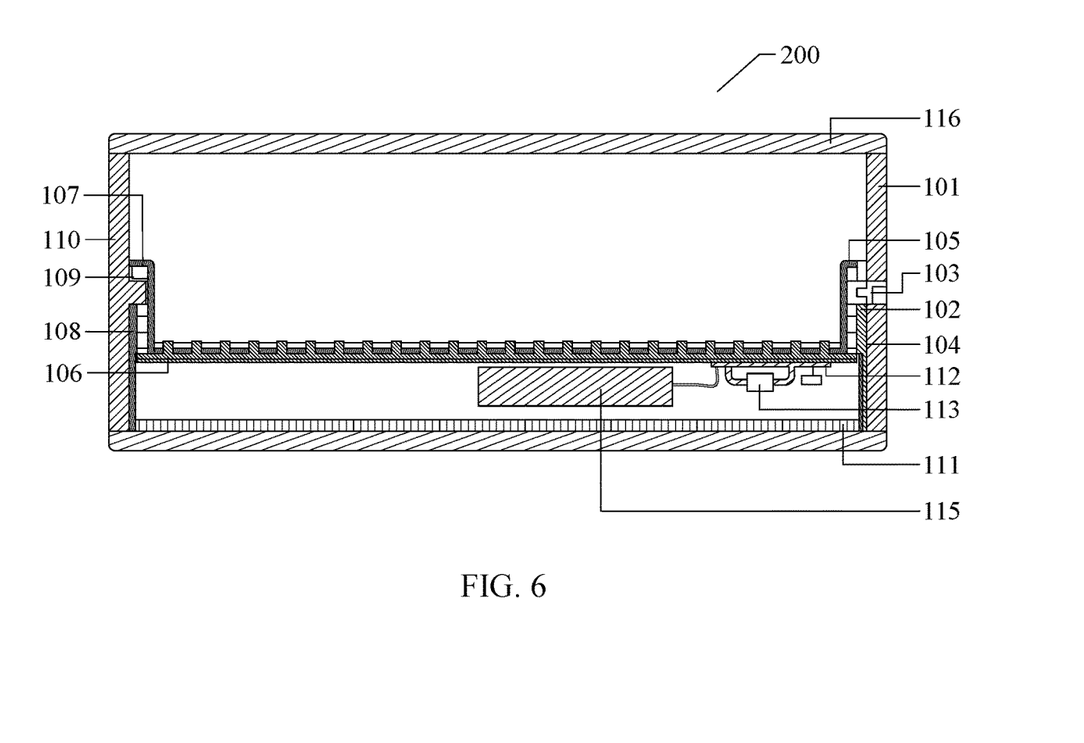
FIG. 6 is a cross-sectional view of the phototherapy body roller according to the second embodiment of the present disclosure.

Further, referring to FIG. 4 to FIG. 6, a phototherapy body roller 200 is shown according to a second embodiment of the present disclosure. The phototherapy body roller 200 includes a left cover 101, a left bearing 102, a power interface 103, a left gravity hammer Oil 104, a left cap 105, a light board 106, a right cap 107, a right gravity hammer 108, a right bearing 109, a right cover 110, a light housing 111, a control board 112, a power switch 113, a battery 115, and an outer casing 116. The power interface 103, the control board 112 and the power switch 113 are connected by wires, and the power supply unit is used to supply power to the light board 106. Further, the left bearing 102, the left gravity hammer 104, the right gravity hammer 108, and the right bearing 109 constitute a balancing device. The function of the balancing device is to ensure that the luminous surface of the light board 106 is always facing upwards.

The left cover 101 has a mounting post at the center axis, and is assembled with an inner ring of the left bearing 102, and is mirror-polished by a metal material so that the left bearing 102 can be operated at a high speed. Further, the outer ring of the left cover 101 is fixed inside the outer casing 116.

The inner ring of the left bearing 102 is assembled with the mounting post of the left cover 101, and the outer ring of the left bearing 102 is fixedly mounted with the left gravity hammer 104.

The power interface 103 is a safe low-voltage current input interface that supplies power to the entire power supply unit to charge the battery 114.

The upper end of the left gravity hammer 104 has a mounting surface fixed to the outer ring of the left bearing 102 and has a cylindrical surface, and the lower end is a gravity end and is fixedly mounted to the light housing 111. When the outer casing 116 rotates, the gravity end is subjected to the gravitational force of the earth, and the center of gravity is always downward, and cannot be rotated to a position above the horizontal plane of the bearing axis, thereby ensuring that the light surface of the light board 106 fixed thereto is always facing upward.

The left cap 105 and the right cap 107 are serving as a covering function to cover the power cord and the like in their respective sides.

The light board 106 is formed by welding LED lamps or infrared lamps or laser diodes such as the laser diodes on the heat dissipating aluminum substrate, and the light emitting tubes always faces the outer casing 118 that is transparent towards upper side. The light board 106 is fixed to the light housing 111 and is fixed to the left gravity hammer 104 and the right gravity hammer 108 in such a way that is would not be rotated beyond the bearing level.

The upper end of the right gravity hammer 108 has a mounting surface and of cylindrical shape, and is fixedly mounted to the outer ring of the right bearing 109, and the lower end is a gravity end and is fixedly mounted to the light housing 111. The right gravity hammer 108 together with the left gravity hammer 104 ensures that when the inner ring of the left bearing 102 and right bearing 109 rotates, the face of the light board 106 fixed thereto always faces upward.

The inner ring of the right bearing 109 is assembled with the mounting post of the right cover 110, and the outer ring is fixedly mounted with the right gravity hammer 108.

The right cover 110 has a mounting post at the central axis, and is assembled with the inner ring of the right bearing 109, and is mirror-polished by a metal material so that the right bearing 109 can be operated at a high speed. The outer ring of the right cover 110 is fixed within the outer casing 116.

The light housing 111 is used for fixing the light board 106, and has a high heat dissipation coefficient metal material and is light in weight.

The control board 112 is loaded with control software, including a sophisticated and high-speed central microprocessor and its electronic components.

The power switch 113 adopts a vibration switch, which generates vibration when the phototherapy body roller 200 rotates, thereby starting up, and the software loaded on a microprocessor sets the working time and program after the power is turned on. The power switch 113 can also adopt a touch switch to be turned on by a skin touch and the touch switching is high in sensitivity and high in reliability. The power switch 113 can also be a pressure sensor switch. When the phototherapy body roller 200 is used, the human body will be pressed on the phototherapy body roller 200 and is automatically turned on by the touch force.

The battery 115 is made of a high polymer battery, has a small volume and a large capacity, and has a high safety factor of explosion protection, and is charged through the power interface 102.

The outer casing 116 is a fully transparent outer casing, which adopts a highly transparent soft material to meet biocompatibility requirements and is in comfortable contact with human skin.

When in use, the outer casing 116 rotates to drive the inner rings of the left cover 101 and the right cover 110 plates and the left bearing 102 and the right bearing 109 fixed thereto. At this time, the outer ring the left bearing 102 and the right bearing 109 is assembled with the left gravity hammer 104 and right gravity hammer 108 respectively. Further, left gravity hammer 104 and right gravity hammer 108 under the action of gravity goes downward with their respective lower ends which are gravity ends and do not allows rotate the light board to reach the bearing axis position. The light board 106 and the light housing 111 are fixed to the gravity end so that the direction of the light board 106 is maintained upward.

In other embodiments, the balancing device can adopt other structures, such as the gravity hammer can be directly fixed under the vertical line of the center of gravity of the light board or the light housing, which can also ensure that the luminous tube on the entire light board is always facing upward. It is also possible to achieve the purpose that the light-emitting tubes are always facing upward by using the light board floating on the liquid surface. According to the purpose of the present invention, those skilled in the art can use other existing technical methods to realize the technical function that the luminous tube is always facing upward. The implementations in the foregoing first embodiment and the second embodiment are simple in structure, reliable in operation and are preferred.

With a balancing device, the light source is always facing the upper part of the phototherapy body roller, which saves energy and does not cause light pollution, and is environmentally friendly. Further, the light emitting tubes are plurality of LEDs or light-emitting diodes.

The above is a further detailed description of the present invention in conjunction with the specific embodiments, and the specific implementation of the present invention is not limited to the description. For those skilled in the art to which the present invention pertains, a number of simple derivations or substitutions may be made without departing from the spirit and scope of the present invention.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not limited to the particular embodiment disclosed, but that the present disclosure will include all embodiments that fall within the scope of the appended claims.

What is claimed is:

1. A phototherapy body roller comprises:
a rigid body having at least one transparent portion;
a plurality of light emitting tubes mounted on a light board accommodated inside the rigid body;
a balancing assembly attached to the light board;
wherein the plurality of light emitting tubes facing towards the at least one transparent portion of the rigid body; and
wherein, the rigid body is rotatable with respect to the light board;
wherein the balancing assembly includes a rotary disk, a gyroscope, a motor, and a bearing:
wherein the gyroscope is electrically connected to a control board and the motor, and is fixedly mounted with the light board;

the rotary disk is connected to the rigid body through the bearing;

a light housing is fixed to the rotary disk, and a center line of the light board is coincident with a central axis of rotation of the rotary disk; and wherein, the motor is mounted coaxially with the bearing and a central axis of the rotary disk, and an output shaft thereof is fixedly mounted with the rotary disk or the light housing.

2. The phototherapy body roller according to claim 1, wherein the rigid body is made of fully transparent material in order to allow light to pass through it.

3. The phototherapy body roller according to claim 1, wherein the rigid body is a cylindrical outer casing or a spherical outer casing.

4. The phototherapy body roller according to claim 1, wherein the plurality of light emitting tubes are light-emitting diodes (LEDs).

5. The phototherapy body roller according to claim 1, wherein the light board is attached to a power supply unit including a power switch, a battery, and a control board, wherein the control board is connected to the battery and the power switch through a conductive line.

6. The phototherapy body roller according to claim 5, wherein the power switch is a vibration switch, a skin touch switch or a pressure sensor switch.

7. The phototherapy body roller according to claim 1, wherein the balancing assembly is mounted inside the rigid body and the light board is fixedly mounted on the balancing assembly.

8. The phototherapy body roller according to claim 1, wherein the light board is simultaneously revolving with a rotary disk and facing towards the at least one transparent portion of the rigid body.

9. The phototherapy body roller according to claim 1, wherein the balancing assembly further includes a gravity hammer and a bearing, the gravity hammer has a lower end and an upper end;

the lower end of the gravity hammer is a gravity end, and the upper end of the gravity hammer has a cylindrical surface;

further, the cylindrical surface of the upper end of the gravity hammer is fixedly mounted with a rotating surface of the bearing, and an outer surface of the bearing is fixedly mounted with the rigid body; and wherein the light board is fixedly mounted with the gravity end of the gravity hammer.

* * * * *